United States Patent [19]

Young

[11] Patent Number: 4,823,611

[45] Date of Patent: Apr. 25, 1989

[54] CERAMIC TILE SHEAR TESTING APPARATUS AND METHOD

[76] Inventor: Robert T. Young, 201 E. Ranchwood Circle, Oklahoma City, Okla. 73160

[21] Appl. No.: 122,048

[22] Filed: Nov. 18, 1987

[51] Int. Cl.⁴ ............................................. G01N 3/24
[52] U.S. Cl. ...................................................... 73/842
[58] Field of Search ................ 73/842, 841, 845, 825, 73/150 A; 254/93 R

[56] References Cited

U.S. PATENT DOCUMENTS

| | | | |
|---|---|---|---|
| 2,353,056 | 7/1944 | Martindell | 265/14 |
| 2,667,069 | 1/1954 | Ramos et al. | 73/91 |
| 2,667,781 | 2/1954 | Barrett | 73/101 |
| 2,674,124 | 4/1954 | Barrett | 73/101 |
| 2,675,699 | 4/1954 | Tilden | 73/101 |
| 2,959,051 | 11/1960 | Simek et al. | 73/101 |
| 3,026,721 | 3/1962 | Ensor et al. | 73/101 |
| 3,090,225 | 5/1963 | Hollar et al. | 73/101 |
| 3,253,461 | 5/1966 | Blanchard et al. | 73/150 |
| 3,376,736 | 4/1968 | Emery | 73/101 |
| 4,012,947 | 3/1977 | Tiegel | 73/101 |
| 4,346,602 | 8/1982 | Gould et al. | 73/842 |

FOREIGN PATENT DOCUMENTS 3317609 3/1985 Fed. Rep. of Germany ... 73/862.42

Primary Examiner—Jerry W. Myracle
Attorney, Agent, or Firm—Laney, Dougherty, Hessin & Beavers

[57] ABSTRACT

A ceramic tile shear testing apparatus and method of use. The apparatus includes a frame with a hydraulic cylinder for moving a shearing member extending outwardly of the frame. The apparatus may be placed on a bonding layer on a working surface adjacent a tile to be tested and the hydraulic cylinder actuated to apply a force to the tile in a direction parallel to the working surface sufficient to break the bond holding the tile to the surface. Pressure in the hydraulic cylinder may be measured when the shear occurs as a correlation of the shear strength of the bond.

20 Claims, 2 Drawing Sheets

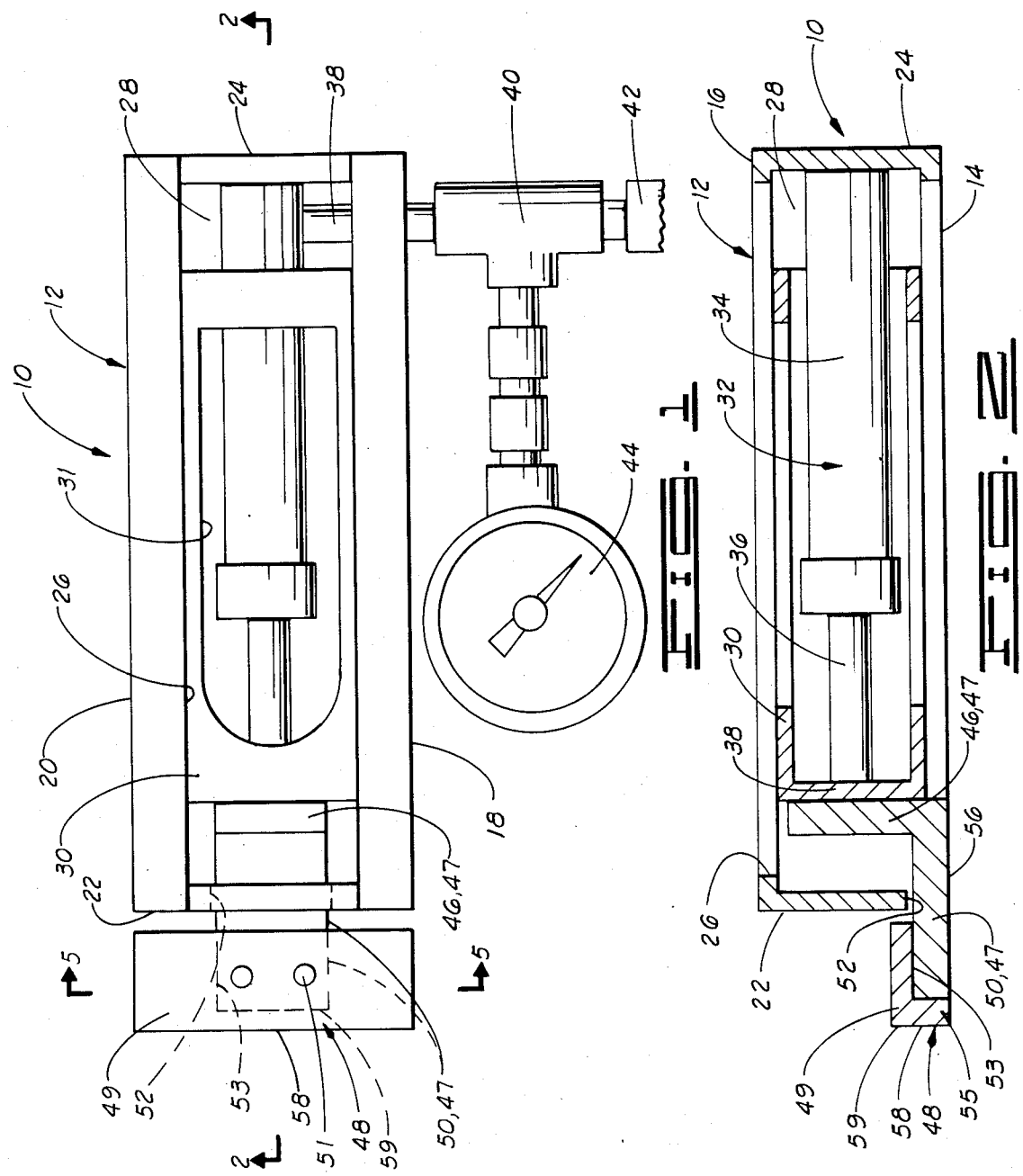

CERAMIC TILE SHEAR TESTING APPARATUS AND METHOD

BACKGROUND OF THE INVENTION

1. Field of the Invention

This invention relates generally to a method and apparatus for shear testing of bonding materials for objects such as ceramic tiles, and more particularly, to an apparatus and method for in-place testing of a tile bonded to a working surface.

2. Description of the Related Art

A number of shear testing devices are known in the art. Some prior art patents disclose a method and apparatus for shear testing bonding material on a test piece or article which has been removed for such purpose from its working position. Examples are U.S. Pat. Nos. 2,353,056 to Martindell; 2,667,781 and 2,674,124 to Barrett; 3,376,736 to Emery, Jr.; 3,026,721 to Ensor et al.; and 2,675,699 to Tilden.

U.S. Pat. No. 2,667,781 to Barrett relates to an apparatus for testing a shear strength of a bond of a brake lining adhesively bonded to a brake shoe. A bonded brake shoe is set on supporting surfaces adjacent a U-shaped slot designed to receive a portion of the brake shoe, with one edge-face of the shoe abutted against a shoulder. Air pressure is then applied to a chamber, which pushes a diaphragm and attached ram forward, resisted by a tension spring. A serrated pressure applying element at a forwardly projecting end of the ram is advanced against a second edge-face of the brake lining until shearing occurs.

In a known device for bench testing the shear strength of a bond holding a tile to a surface, two test tile portions are bonded together with a bonding joint such that the two tiles are offset from one another. One tile is placed into engagement with a portion of the frame of the apparatus, and an opposite edge of the second tile engages a piston actuated by a hydraulic cylinder. The piston forces one tile toward the other until shearing of the bond occurs. A pressure gauge is provided for measuring the pressure in the hydraulic cylinder corresponding to the shearing force applied.

The primary disadvantages with these prior apparatus are the inconvenience involved in preparing the test pieces and the inaccuracy resulting from bench testing rather than testing on an actual working surface.

In U.S. Pat. No. 3,090,252 to Hollar et al., a test button on a panel is prepared in the skin of the panel by removing material in an annular region around the button to a depth of the thickness of the skin. An adaptor is placed against an edge of the test button and shears the test button when actuated. A pressure-actuated piston presses against a load arm to which the adaptor is attached. The load arm pivots about a pin in an upper portion of a frame, and forces the adaptor forward until the test button is sheared.

Although the device of Hollar et al. is used to test the button in place, the load arm which transmits the shearing force to the adaptor does so by pivoting about the pin. The adaptor thus moves through an arc rather than by moving a shearing member in a direction parallel to the panel as with the present invention.

The present invention overcomes the shortcomings of the prior art by providing an apparatus and method for testing a shear strength of a bond of a tile attached to a working surface by applying a force parallel to the working surface.

SUMMARY OF THE INVENTION

The method of the present invention for shear testing a bond holding a tile to a working surface comprises the steps of removing at least some grouting material adjacent the tile to be tested, applying a force to the tile in a direction substantially parallel to the working surface for shearing the bond, and measuring the force, directly or indirectly, when shear occurs.

The step of removing grouting material preferably comprises removing substantially all of the grouting material between the tile to be tested and at least some adjacent tiles.

The step of applying a force to the tile comprises placing a shearing member into engagement with an edge of the tile and forcing the shearing member against the edge.

The shearing member is preferably a portion of the ceramic tile testing apparatus of the present invention which also comprises a frame having a side positionable adjacent a bonding layer on the working surface with the shearing member movable with respect to the frame. The shearing member preferably has a side disposed substantially coplanar with the side of the frame. The apparatus further comprises reciprocating means attached to the frame for moving the shearing member with respect to the frame and thereby applying the force to the tile to be tested.

In the preferred embodiment, the reciprocating means comprises a hydraulic cylinder connectable to a pressure source, and the apparatus further comprises means for measuring a pressure in the hydraulic cylinder.

An end of the frame preferably defines at least a portion of a slot therein through which a portion of the shearing member outwardly extends.

The shearing member comprises a bracket portion and an adapter portion attachable to the bracket portion, the adapter portion being one of a plurality of interchangeable adapter portions. The bracket portion is of substantially L-shaped configuration having a transverse portion and a longitudinal portion extending away from the reciprocating means. The apparatus preferably further comprises a piston slidably disposed in the frame, and the transverse portion of the bracket portion is attached to the piston. The reciprocating means is adapted for engaging an end of the piston for moving it and the bracket portion.

The method of testing preferably further comprises the steps of removing at least one tile between the tile to be tested and another tile, and placing the apparatus into engagement with an edge of the other tile. The step of measuring the force comprises measuring the pressure in the hydraulic cylinder. The width of the shearing member is adjusted such that the shearing member is at least as wide as the edge of the tile to be tested. This may include selecting one of the interchangeable adapters which is at least as wide and as high as the edge of the tile.

It is an important object of the present invention to provide an accurate and convenient method and apparatus for testing a shear strength of a bond of a tile attached to a working surface by a bonding material.

It is another object of the invention to provide a tile testing apparatus for testing a tile in place on a working surface.

It is a further object of the invention to provide an apparatus for shear testing a tile on a working surface such that a force is applied to the tile substantially parallel to the working surface.

Other objects and advantages of the invention will become apparent as the following detailed description of the preferred embodiment is read in conjunction with the drawings which illustrate such preferred embodiment.

BRIEF DESCRIPTION OF THE DRAWINGS

FIG. 1 shows a view of a preferred embodiment of the testing apparatus of the present invention taken from a side thereof.

FIG. 2 is a cross-sectional view along lines 2—2 in FIG. 1.

DETAILED DESCRIPTION OF THE PREFERRED EMBODIMENT

Figure 3:
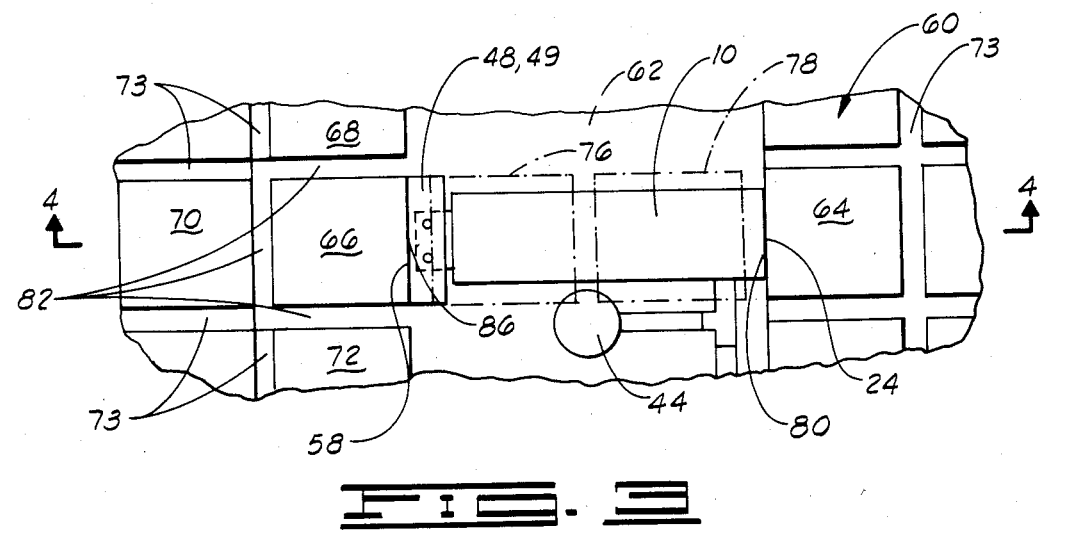
FIG. 3 is a schematic of the tile testing apparatus shown in position for shear testing a tile bonded to a working surface.

Referring now to the drawings, and more particularly to FIGS. 1 and 2, the ceramic tile shear testing apparatus of the present invention is shown and generally designated by the numeral 10. Apparatus 10 includes a frame 12 of generally parallelepiped configuration. Frame 12 has four longitudinally extending sides 14, 16, 18 and 20, and two transverse ends 22 and 24. Any of sides 14, 16, 18 and 20 may have an opening therein such as opening 26 in side 16.

Frame 12 is hollow and defines a substantially rectilinear cavity 28 therein. Slidably disposed in cavity 28 is a piston 30, also of substantially parallelepiped configuration. Piston 30 may also have one or more openings, such as opening 31, therein.

A reciprocating means 32 is disposed in cavity 28 and extends into piston 30. In a preferred embodiment, reciprocating means 32 is characterized as a hydraulic cylinder 32 having a base portion 34 connected to end 24 of frame 12 by a means known in the art. Other reciprocating means could also be used. A reciprocable rod portion 36 of hydraulic cylinder 32 extends from base portion 34 and is adapted to bear against an end 38 of piston 30, but is not necessarily connected to the piston.

Base portion 34 of hydraulic cylinder 32 defines a hydraulic chamber therein of a kind known in the art which is in communication with a nipple 38 which extends from base portion 34 and externally of frame 12, as best shown in FIG. 1. Nipple 38 is connected to a tee 40 which is in turn connected to a line 42 from a pressure source of a kind known in the art. A pressure gauge 44 is also connected to tee 40. It will be seen that by supplying pressure from the pressure source through line 42, hydraulic cylinder 32 may be actuated such that rod portion 36 thereof may be extended. When rod portion 36 comes in contact with piston 30, the piston is thus moved within cavity 28 toward end 22 by the actuation of hydraulic cylinder 32.

Attached to end 38 of piston 30 is a transverse portion 46 of a bracket 47 forming at least a portion of a shearing member 48. It will be seen that shearing member 48 thus moves with piston 30 when hydraulic cylinder 32 is actuated. Preferably, hydraulic cylinder 32 is positioned in cavity 28 such that it is as near side 14 of frame 12 as possible in order to minimize the bending moment exerted on transverse portion 46 of bracket 47 of shearing member 48.

Bracket 47 is of substantially L-shaped cross-sectional configuration, as seen in FIG. 2, and has a longitudinal portion 50 extending from transverse portion 46. Longitudinal portion 50 extends outwardly from frame 12 through a slot 52 in end 22 of frame 12. Slot 52 is formed such that a portion of side 14 of frame 12 is open. Thus, as shown in the cross section of FIG. 2, a substantially transverse edge 54 extends from side 14 adjacent transverse portion 46 of bracket 47.

Figure 5:
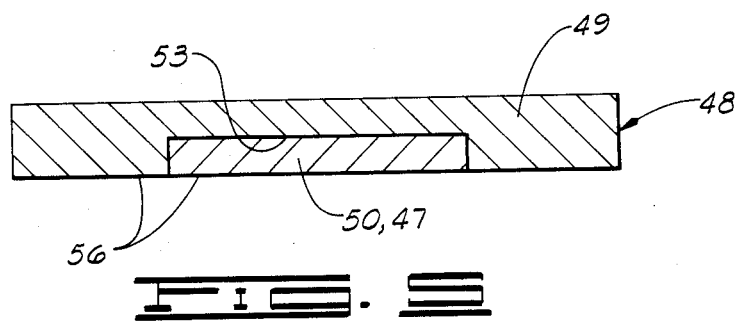
FIG. 5 shows a cross-sectional view of a shearing member used in the invention taken along lines 5—5 of FIG. 1.

An adapter 49, also considered to be a portion of shearing member 48, may be attached to longitudinal portion 50 of bracket 47 by screws 51 of a kind known in the art. Adapter 49 defines a notch 53 therein which is adapted to receive a portion of longitudinal portion 50 of bracket 47, as best seen in FIG. 5. A lip portion 55 of adapter 49 thus is positioned adjacent bracket 47.

Longitudinal portion 50 of bracket 47 and an adjacent surface of adapter 49 form a substantially flat longitudinally extending side 56 of shearing member 48. It will be seen that side 56 of shearing member 48 is substantially coplanar with the outer surface of side 14 of frame 12, as best shown in FIG. 2.

Adapter 49 has an outwardly facing edge 58, and longitudinal portion 50 of bracket 47 similarly has an outwardly facing edge 59. Edges 58 and 59 are adapted for engagement with a tile to be tested depending on the tile size, as hereinafter described. Adapter 49 is preferably interchangeable with adapters of different widths for accommodating various sizes of tile.

Figure 4:
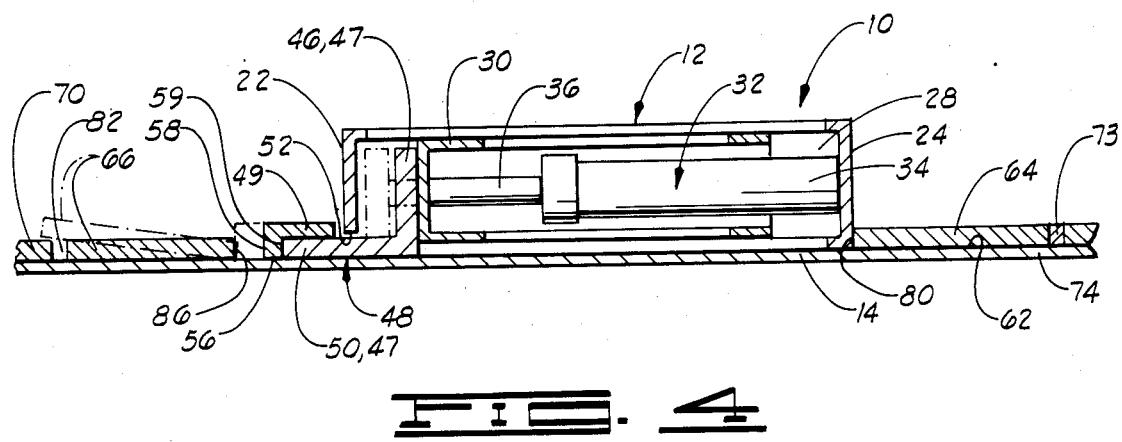
FIG. 4 is a cross section along lines 4—4 of FIG. 3.

Referring now to FIGS. 3 and 4, operation of shear testing apparatus 10 and a method of shear testing a tile on a working surface will be discussed. A tile array 60 is attached to a working surface 62, such as a wall or floor, by a bonding material of a kind known in the art, such as mortar. Tile array 60 comprises a plurality of tiles, including tiles 64, 66, 68, 70 and 72, as shown in FIG. 3. The tiles are separated by a grouting material, generally indicated by the reference numeral 73. Grout 73 is generally made of different material than the bonding material which attaches the tiles to working surface 62.

As seen in FIG. 4, tile array 60 is bonded to working surface 62 by bond 74 which is made of the bonding material already mentioned. When tile array 60 is properly affixed to working surface 62, the bonding material forms a substantially continuous layer between the tiles and the working surface as is known in the art.

In order to test the strength of bond 74 holding a single tile, such as tile 66, to working surface 62, it is necessary to clear out a working area adjacent tile 66. As best seen in FIG. 3, all of the tiles, such as tiles 76 and 78, between tile 64 and tile 66 are removed. Obviously, the number of tiles removed depends on tile size, but at least one tile must be removed. Preferably, bond 74 is left in place on working surface 62 between tiles 64 and 66.

Testing apparatus 10 may be placed on the bond layer on working surface 62 between tiles 64 and 66. As best seen in FIG. 4, side 14 of frame 12 of apparatus 10 is placed in contact with bond 74 on working surface 62. End 24 of frame 12 of apparatus 10 is preferably placed in contact with adjacent edge 80 of tile 64. At least some, and preferably substantially all, of grout 73 adjacent tile 66 and separating it from tiles 68, 70 and 72 is removed such that a substantially C-shaped gap 82 is defined adjacent tile 66. Thus, only the bonding material is still in contact with tile 66, and tile 66 is isolated from the other tiles.

Hydraulic cylinder 32 is actuated sufficiently to place edge 58 of adapter 49 in contact with adjacent edge 86 of tile 66 if adapter 49 is used. Preferably, edge 58 is at least as wide and as high as edge 86 of tile 66. In this way, shearing member 48 bears evenly across all of edge 86 of tie 66. As already indicated, adapter 49 is interchangeable with other adapters of different lengths to accommodate different sizes of tile 66. Further, if tile 66 is sufficiently small, adapter 49 may be omitted such that only edge 59 of longitudinal portion 50 of bracket 47 is needed to engage the tile to be tested. Again, edge 59, when so used, is preferably at least as wide and as high as the edge of the tile being tested. When used, either edge 58 or 59 may be considered as an edge of shearing member 48. Thus, it will be seen that shearing member 48, with or without adapter 49, is adjustable for different sizes of tile.

It will be seen that further actuation of hydraulic cylinder 32 to outwardly reciprocate rod portion 36 from base portion 34 forces shearing member 48 against edge 86 of tile 66 with a purely longitudinal motion, substantially parallel to working surface 62. When sufficient pressure has been applied to hydraulic cylinder 32, as indicated on pressure gauge 44, the portion of bond 74 connecting tile 66 to working surface 62 will shear so that the tile is moved, such as indicated by the phantom lines in FIG. 4, from its original position. While this operation is taking place, the operator can measure the pressure on pressure gauge 44 when the shear occurs, thus providing a measurement which can be correlated with the shear strength of bond 74. Other measuring means could also be employed. Grout 73 around tile 64 and the adjacent tiles prevent tile 64 from breaking loose instead of tile 66. In other words, once isolated, tile 66 is the weakest point.

After the test is complete, rod portion 36 of hydraulic cylinder 32 may be reciprocating back toward base portion 34. Piston 30 and shearing member 48 attached thereto may then be manually moved back to their initial position.

Similar tests may be carried out on other tiles as desired so that an average shear strength value of the bonding material may be obtained. The obvious advantage of this apparatus over the previously known ceramic tile shear testing apparatus is that it is designed to function to test a tile, such as tile 66, which is still actually in place on its original working surface 62. This provides a much more realistic shear strength value for the bonding material than can be obtained by bonding of two sample pieces of tile and bench or laboratory testing the bond.

It can be seen, therefore, that the ceramic tile shear testing apparatus and the method described for testing of tiles on a working surface are well adapted to carry out the ends and advantages mentioned as well as those inherent therein. While a presently preferred embodiment of the apparatus and a method of use thereof have been described for the purposes of this disclosure, numerous changes in the arrangement and construction of parts of the apparatus and in the steps of the method may be made by those skilled in the art. All such changes are encompassed within the scope and spirit of the appended claims.

What is claimed is:

1. A method of testing a shear strength of a bond holding a tile to a working surface, said method comprising the steps of:
   removing at least some grouting material adjacent the tile to be tested;
   applying a force to said tile in a direction substantially parallel to said working surface for shearing said bond; and
   measuring said force.

2. The method of claim 1, wherein said step of removing grouting material comprises removing substantially all of said grouting material between said tile and at least some adjacent tiles.

3. The method of claim 1, wherein said step of applying a force to said tile comprises:
   placing a shearing member into engagement with an edge of said tile; and
   forcing said shearing member against said edge.

4. The method of claim 3, wherein said shearing member is a portion of a testing apparatus, said method further comprising the steps of:
   removing at least one tile between said tile to be tested and another tile; and
   placing an end of said apparatus into engagement with an edge of the other tile.

5. The method of claim 4, wherein:
   said apparatus comprises a hydraulic cylinder for moving said shearing member; and
   said step of measuring said force comprises measuring a pressure in said hydraulic cylinder.

6. The method of claim 3 further comprising adjusting a width of said shearing member such that said shearing member is at least as wide as said edge of said tile.

7. The method of claim 6 wherein:
   a portion of said shearing member includes one of a plurality of interchangeable adapters; and
   said step of adjusting a width of said shearing member comprises selecting said one of said adapters which is at least as wide as said edge of said tile.

8. An apparatus for shear testing a bonding strength of a tile bonded to a working surface, said apparatus comprising:
   a frame having an outer side positionable adjacent a bonding layer on said working surface;
   a shearing member movable with respect to said frame and having a side substantially coplanar with said outer side of said frame such that said side of said shearing member may be moved along said bonding layer on said working surface; and
   reciprocating means attached to said frame for moving said shearing member along said bonding layer on said working surface and with respect to said frame whereby a force may be applied to an edge of said tile.

9. The apparatus of claim 8, wherein said reciprocating means comprises a hydraulic cylinder connectable to a pressure source.

10. The apparatus of claim 9 further comprising means for measuring a pressure in said hydraulic cylinder.

11. The apparatus of claim 8, wherein a portion of said shearing member extends outwardly from said frame.

12. The apparatus of claim 11, wherein an end of said frame defines at least a portion of a slot therein through which said portion of said shearing member extends.

13. An apparatus for shear testing a bonding strength of a tile bonded to a working surface, said apparatus comprising:
- a frame having a side positionable adjacent a bonding layer on said working surface;
- a shearing member movable with respect to said frame and having a side substantially coplanar with said side of said frame, said shearing member comprising:
  - a bracket portion; and
  - an adapter portion attachable to said bracket portion, said adapter portion being one of a plurality of interchangeable adapter portions; and
- reciprocating means attached to said frame for moving said shearing member with respect to said frame whereby a force may be applied to an edge of said tile.

14. The apparatus of claim 13 further comprising a piston slidably disposed in said frame, said bracket portion being attached to said piston, and said reciprocating means being adapted for engaging an end of said piston.

15. The apparatus of claim 14 wherein said bracket portion is of substantially L-shaped configuration having a transverse portion attached to said piston and a longitudinal portion extending away from said reciprocating means.

16. The apparatus of claim 13 wherein at least one of said bracket portion and said adapter portion has an edge at least as wide and as high as an edge of said tile.

17. In an apparatus for testing a shear strength of a bond holding a tile to a working surface wherein the apparatus includes a frame having a side, a piston slidably disposed in said frame and reciprocating means for bearing against said piston, the improvement which comprises:
- said frame defining a slot in an end thereof; and
- a shearing member attached to said piston and having a longitudinal portion extending from said frame through said slot defined in said side of said frame.

18. The apparatus of claim 17, wherein said longitudinal portion of said shearing member has a side substantially coplanar with said side of said frame.

19. The apparatus of claim 18, wherein said shearing member has a transverse portion substantially perpendicular to said side of said shearing member, said transverse portion being attached to said piston.

20. The apparatus of claim 17 wherein said shearing member comprises an adapter attachable to said longitudinal portion, said adapter being one of a plurality of interchangeable adapters of different widths.

* * * * *